US008933245B2

(12) United States Patent
Yarosh

(10) Patent No.: US 8,933,245 B2
(45) Date of Patent: Jan. 13, 2015

(54) PRESERVATION OF ERGOTHIONEINE

(71) Applicant: Daniel B. Yarosh, Merrick, NY (US)

(72) Inventor: Daniel B. Yarosh, Merrick, NY (US)

(73) Assignee: ELC Management LLC, New York, NY (US)

( * ) Notice: Subject to any disclaimer, the term of this patent is extended or adjusted under 35 U.S.C. 154(b) by 0 days.

(21) Appl. No.: 13/671,955

(22) Filed: Nov. 8, 2012

(65) Prior Publication Data

US 2014/0128615 A1     May 8, 2014

Related U.S. Application Data

(62) Division of application No. 12/362,594, filed on Jan. 30, 2009, now Pat. No. 8,410,156.

(51) Int. Cl.
*A61K 47/12*     (2006.01)
*A61K 8/00*     (2006.01)
*A61K 8/30*     (2006.01)

(52) U.S. Cl.
CPC ........................................ *A61K 8/00* (2013.01)
USPC ........ 548/324.1; 514/398; 514/556; 514/709; 514/580

(58) Field of Classification Search
USPC ................. 514/398, 556, 709, 580; 548/324.1
See application file for complete search history.

(56) References Cited

U.S. PATENT DOCUMENTS

| | | | |
|---|---|---|---|
| 3,989,498 | A | 11/1976 | Cox |
| 4,357,362 | A | 11/1982 | Barker |
| 4,845,289 | A | 7/1989 | Ries et al. |
| 5,078,913 | A | 1/1992 | Bennett |
| 5,137,982 | A | 8/1992 | Bennett |
| 5,236,986 | A | 8/1993 | Sakuta |
| 5,409,769 | A | 4/1995 | Fukumoto et al. |
| 5,412,004 | A | 5/1995 | Tachibana et al. |
| 5,438,151 | A | 8/1995 | Yadan et al. |
| 5,811,487 | A | 9/1998 | Schultz, Jr. et al. |
| 5,814,233 | A | 9/1998 | Starkey et al. |
| 5,837,793 | A | 11/1998 | Harashima et al. |
| 6,479,533 | B1 | 11/2002 | Yarosh |
| 2004/0047823 | A1 | 3/2004 | Catroux et al. |
| 2006/0034875 | A1 | 2/2006 | Nakanishi et al. |
| 2006/0263400 | A1* | 11/2006 | Bissett ........................... 424/401 |

FOREIGN PATENT DOCUMENTS

| | | |
|---|---|---|
| CA | 2609690 | 11/2006 |
| CA | 2680223 | 9/2008 |
| EP | 0483426 | 5/1992 |
| JP | 60-136506 | 7/1985 |
| JP | 1-238866 | 9/1989 |
| JP | 2003-533462 | 11/2003 |
| WO | WO2004/024798 | 3/2004 |

OTHER PUBLICATIONS

Shahidi, F. et al. Antioxidants: Regulator Status in Bailey's Industrial Oil and Fat Products, Sixth Edition, Ed. Shahidi, F. (Wiley: New York 2005), pp. 491-512.*
Mann, T. The Biochemistry of Semen in Methuen's Monographs on Biochemical Subjects, Eds. Peters, R. and Young, F. G. (Wiley: New York 1954).*
H. Heath, A. Lawson and C. Rimington; "2-Mercaptoglyoxalines; Part I; The Synthesis of Ergothioneine"; (1951); J. Chem. Soc.; pp. 2215-2217.
Philip E. Hartman; "Ergothioneine as Antioxidant"; Methods Enzymology; vol. 186; pp. 310-318; 1990.
H. Heath, and G. Toennies; "The Preparation and Properties of Ergothioneine Disulphide"; J. Chem. Soc.; vol. 68; pp. 204-210; 1958.
PCT International Search Report; Internaitonal Application No. PCT/US2010/021125; Completion Date: Sep. 29, 2010; Mailing Date: Sep. 29, 2010.
PCT Written Opinion of the International Searching Authority, or the Declaration International Application No. PCT/US2010/021125; Completion Date: Sep. 29, 2010; Mailing Date: Sep. 29, 2010.
Oxis International, Inc.; "Compound Monograph; L-Ergothioneine; Revision III;" pp. 1-17, Jun. 2003.
Xu, et al.; "Synthesis of L-(+)-Ergothioneine;" J. Org. Chem.; 60:6296-6301; Apr. 1995.
Melville, Donald B.; "Ergothioneine;" Vitamins and Hormones; 17:155-204; pp. 155-204; Dept. of Biochem, Cornell Univ. Medical College; NY; NY; 1959.
Bright, et al.; "Addition Compound of Sulfur Dioxide and Trimethylamine;" Inorganic Syntheses; vol. II; Chapter VI; pp. 159-161; Edited by. W. Conard Fernelius; McGraw-Hill Book Company, Inc.; 1946.

(Continued)

*Primary Examiner* — Joseph Kosack
*Assistant Examiner* — Amanda L Aguirre
(74) *Attorney, Agent, or Firm* — Cynthia R. Miller

(57) ABSTRACT

Compositions comprising ergothioneine and a trimethylamine absorber are provided. Also provided are methods for preventing, reducing or minimizing the fishy, amine odor, due to trimethylamine, that is associated with the processing and/or storage of a preparation containing ergothioneine, by combining with the ergothioneine, during processing or prior to storage, a trimethylamine absorber in an amount sufficient to prevent the detection of any trimethylamine odor by the human nose. A method is further provided for ameliorating the methylamine odor associated with an aqueous ergothioneine-containing preparation after it has developed a fishy trimethylamine odor.

11 Claims, 1 Drawing Sheet

(56) References Cited

OTHER PUBLICATIONS

Balaban, et al.; "Gold and Mercury Derivatives of 2-Thiolglyoxalines. Mechanism of the Oxidation of 2-Thiolglyoxalines to Glyoxalines.;" J. Chem. Soc.; pp. 1858-1874; May 1927.

Booth, et al.; "Degradation of Ergothioneine by Cell-Free Extracts of Alcaligenes Faecalis;" II. Production of Glutamic Acid; Dept. of Bacteriology, Univ. of So. California; Los Angeles; CA; pp. 654-657; Oct. 1962.

Barnet; Company Brochure; Barnet Products Corporation; Engelwood Cliffs; NJ; Thiotaine Dossier; Presents: "Skin Energy Supplement; Increasing Oxygen Use & Energy From Mitochondria;" AGI Dermatics; Thiotaine; pp. 1-16; 2003.

Asmus, et al.; "One-electron oxidation of ergothioneine and analogues investigated by pulse radiolysis: redox reaction involving ergothioneine and vitamin C;" Biochem. J.; vol. 315; pp. 625-629; 1996.

http://skincarerx.com/Remergent-Clarifying-Concentrate-2.html; SkinCareRx; Home/Remergent/Cleanser & Treatments/Remergent Clarifying Concentrate 2, Retrieved online Jan. 29, 2010.

http://www.gnpd.com; Mintel gnpd; Platinum Deep Treatment; Record ID: 983882; Cosmé Proud; Cosmé Proud; Skincare; Face/Neck Care; USA; Oct. 2008.

http://www.gnpd.com; Mintel gnpd; Ultimate Night Repair Cream; Record ID: 795006; Valeant Pharmaceuticals; Kinerase; Skincare; Face/Neck Care; UK; Aug. 2007.

http://www.gnpd.com; Mintel gnpd; Ultimate Night Repair Cream; Record ID: 793739; Valeant Pharmaceuticals; Kinerase; Skincare; Face/Neck Care; France; Jun. 2007.

http://www.gnpd.com; Mintel gnpd; Ultimate Night Moisturizer; Record ID: 715463; Valeant Pharmaceuticals; Kinerase; Skincare; Face/Neck Care; USA; May 2007.

http://www.gnpd.com; Mintel gnpd; NoAge Crème Facial Care; Record ID: 177180; Parfums Christian Dior; Christian Dior; Skincare; Face/Neck Care; Germany; Nov. 2002.

http://www.gnpd.com; Mintel gnpd; Face Emulsion; Record ID: 104230; Lancaster; Lancaster $O^2$ Re-Oxygen; Skincare; Face/Neck Care; France; Jul. 2001.

http://www.gnpd.com; Mintel gnpd; Re-Oxygen Treatment Range; Record ID: 105511; Lancaster; Lancaster; Skincare; Face/Neck Care; Spain; Jul. 2001.

http://gnpd.com; Mintel gnpd; Eye Contour Care; Record ID: 97117; Lancaster; Re-Oxygen; Skincare; Eye Care; Italy; May 2001.

Jocelyn, P.C.; The Distribution of Ergothioneine in Blood as Determined by a New Method of Estimation; Department of Clinical Chemistry; University of Edinburgh; Received Apr. 28, 1958); vol. 70; Bioch.; pp. 656-660; 1958.

\* cited by examiner

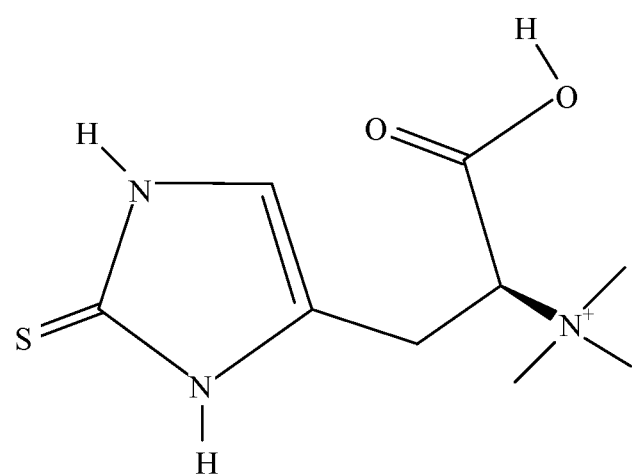
PRIOR ART

PRESERVATION OF ERGOTHIONEINE

The present application is a divisional of U.S. Ser. No. 12/362,594, filed Jan. 30, 2009, now U.S. Pat. No. 8,410,956, which issued Apr. 2, 2013.

FIELD OF THE INVENTION

The present invention relates to the preparation of ergothioneine or ergothioneine-containing mixtures that ameliorates changes in the odor of the product during processing and/or storage. In particular, the preparation involves the addition of acids and/or sulfur dioxide donors that reduce or prevent the formation of trace volatile compounds to which the human nose is particularly sensitive. The resulting preparations retain an innocuous odor even after challenge with conditions, such as alkali or storage over time, which would otherwise produce fishy, amine odors in ergothioneine solutions or ergothioneine-containing mixtures. The acids and/or sulfur dioxide donor compounds may also be added to the ergothioneine solutions or ergothioneine-containing mixtures after the detection of the odor to reduce or eliminate the volatile trace compounds to which the human nose is sensitive.

BACKGROUND OF THE INVENTION

Ergothioneine is a non-essential L-amino acid found naturally in the body. It is a very strong antioxidant, and because it is a carnitine analog, it may also have activity in aerobic ATP production. It is synthesized by types of fungi but not mammals, who must acquire it in their diet. They do so by direct consumption of fungi such as mushrooms, or from grains which have themselves taken up ergothioneine from fungi in their roots. Methods for the laboratory preparation of synthetic ergothioneine have been described in, for example, H. Heath, A. Lawson and C. Rimington. "2-Mercaptoglyoxalanes. Part I. The synthesis of Ergothioneine", *J. Chem. Soc.* (1951) pp 2215-2217 and in U.S. Pat. No. 5,438,151.

It has been observed that ergothioneine is quite stable at acidic pH. At pH 5 a 0.05% solution remains within 1% of its concentration after heating 40 C for 60 days. However, the reports of its stability in alkali are mixed in the literature. See, for example, Philip Hartman. "Ergothioneine as antioxidant", *Methods Enzymol.* 186:310-318, 1990 at p. 311 (" . . . the sulfur atom of Ergothioneine is remarkably stable to alkali"); H. Heath and G. Toennies. "The preparation and properties of Ergothioneine disulphide", *J. Chem. Soc.* pages 204-210, (1958) at p. 204 ("the sulphur is completely unaffected by boiling 50% aqueous potassium hydroxide."); Oxis International, Inc. *Compound Monograph* "L-Ergothioneine. Revision III", at p. 4 ("at physiological pH LE [L-Ergothioneine] does not auto-oxidize and is therefore very stable in aqueous solution." . . . "remarkably stable to strong alkali"); and Jin-zhu Xu and Jean Claude Yadan. "Synthesis of L-(+)-Ergothioneine", *J. Org. Chem.* 60:6296-6301, 1995 at p. 6296 ("this explains its stability toward oxidative dimerization").

On the other hand, see U.S. Pat. No. 5,438,151, at column 1, line 40 ("the very ready β-elimination of the trimethylammonium group in alkaline medium"); Donald Melville. "Ergothioneine. Vitamins and Hormones", 17:155-204, 1959, at p. 161 ("When Ergothioneine was boiled with 50% KOH solution, trimethylamine was evolved and a yellow acid $C_6H_6O_2N_2S$ was formed"), and at p. 165 ("The two most characteristic chemical reactions of Ergothioneine are the ready oxidation of the sulfur atom and the lability of the trimethylammonium radical toward alkali . . . the formation of thiolurocanic acid and trimethylamine by the treatment of Ergothioneine with hot, concentrated alkali has already been considered.").

Ergothioneine and its solutions have no odor, despite the presence of sulfur, because the sulfur is in the thione conformation (C=S), which has no odor, rather than the sulfhydryl conformation (C—SH), which has the odor of rotten eggs. The literature does not mention the appearance of any odor during storage under any conditions. In fact, European Patent No. EP0483426 describes ergothioneine as one of the preferred ingredients in a deodorant composition for topical application to the skin. The contents of the documents cited herein are incorporated herein by reference in their entirety.

The inventor has observed that a cosmetic formulation containing 0.3% ergothioneine at pH 4.2-5.0, stored over several months at room temperature, when rubbed onto a person's skin, presented a fishy, amine odor to that person. Other cosmetic formulations with more dilute solutions of 0.001% or 0.0005% at pH 7 also produced a fishy, amine odor when rubbed onto a person's skin. However, in the cases of the more dilute solutions, the odor was detected by some individuals and not others. The odor was produced by stored samples which retained the same concentration of the ergothioneine as they did initially.

The fishy, amine odor associated with ergothioneine is a disadvantage in commercialization, particularly in oral pharmaceuticals, injectable pharmaceuticals, topical pharmaceuticals, cosmetic products, nutritional supplements, nutritional drinks, and other consumer products.

Those skilled in the art have found the removal or prevention of the fishy, amine odor in aqueous solutions to be a particularly difficult problem. U.S. Pat. No. 5,814,233 describes a method for remediating methyl amine odors in aqueous systems using a compound with amide or imide functionality, such as a hydantoin composition, in the presence of hydrogen peroxide. The patent further proposes reacting choline with hydantoin and hydrogen peroxide. In U.S. Pat. Nos. 5,137,982 and 5,078,913, the inventors describe a method for removing odor from a solution containing trimethylamine and choline chloride using polybasic acid to react with the choline chloride. The acids described include strong acids such as sulfuric acid. U.S. Pat. No. 4,845,289 describes a method for the removal or reduction of odor by use of methyl chloride at temperatures above 50° C. As disclosed in the patent, "In these products as well as others, there frequently remains upon completion of the reaction excess trimethylamine which is odiferous and has undesirable toxicological problems. The residual trimethylamine is difficult to remove completely from aqueous system because of its high solubility in water, and extensive purging with an inert gas and/or removal of water is necessary to also remove substantial quantities of amine. This can be a time-consuming and energy intensive process."

In addressing this concern, the initial assumption of the inventor was that ergothioneine dimerizes by forming a disulfide link between two molecules over time, which was not detected by the analytical method. The inventor then reasoned that the dimer reacts on the surface of a person's skin to release a compound that produces an odor. The most widely recognized component of the human body which can produce a fishy, amine smell is choline, which is a component of prevalent skin lipids such as phosphatidyl choline. Persons with large amounts of choline in their diets, or who are defective in metabolizing choline, develop a fishy, amine odor on their breaths and their bodies. It was therefore hypothesized by the inventor that the reactant, perhaps choline, differed from one person's skin to another, which would explain why some people detected the odor after rubbing it on their skin and others did not. In addition, it was theorized that the reaction required a few seconds of heat from the skin, which would explain why the odor appeared in a delayed fashion.

However, the inventor has now appreciated that the source of the odor associated with the manufacture and storage of ergothioneine is not related to the presence of choline, and that none of the methods of the prior art are useful in preventing the formation of the odor, produced after application to human skin, of a product that contains ergothioneine but that does not contain choline chloride.

The present invention describes practical methods which have now been discovered to prevent the formation of the odor and/or eliminate the odor, and to thereby remove this hindrance to commercialization.

Without being limited to one particular theory, it is believed that the odor associated with ergothioneine may be caused by the formation of minute quantities of trimethylamine in solution at neutral or even acidic pH over time. Trimethylamine is a gas which has a strong ammonium odor but in trace amounts has a fishy, amine odor. It is produced by rotting fish and other decaying foods. The human nose is sensitive to minute quantities of trimethylamine (odor threshold 25 parts per billion), which probably evolved as a defense mechanism to detect contaminated foods and thus to avoid illness. The gas is formed within the aqueous phase of ergothioneine mixtures and remains dissolved, thus masking the odor when the mixture is smelled directly. However, when the ergothioneine mixture is applied to skin, the aqueous components of the mixture are absorbed and the heat of the skin volatilizes the trimethylamine. This may explain why, after rubbing the mixture onto skin, the odor is detectable only after a few seconds. Therefore, it is theorized that the variation in perception of the odor by people is not a result of differences in their skins or choline content but rather because of the significant differences in olfactory sensitivity in the human population, i.e. the ability to detect trimethylamine in trace amounts. In fact, 5-7% of the human population is unable to smell it at all, a condition called anosmia. HPLC analyses of the ergothioneine concentrations did not detect the reduction in ergothioneine or the formation of trimethylamine because the changes were in trace amounts below the limits of detection of the HPLC, but not below the limit of the human nose to detect trimethylamine.

This observation by the inventor was confirmed by reproducing the fishy, amine odor by boiling 2 mM (0.046%) ergothioneine with 0.1 N NaOH (pH 11.5) for 10 minutes. The odor was not ammonia-like, and was detectable by all persons. This became the assay system used to test agents and procedures for reduction or prevention of the odor.

It now has been discovered by the inventor that certain trimethylamine absorbers, which also may be referred to as binders or conjugators, are able both to prevent the formation of trimethylamine from ergothioneine and to bind to trimethylamine after its formation to prevent it from escaping as a gas detectable by the nose.

In one embodiment of the present invention, the trimethylamine binder is an acid, especially a weak acid.

In a further embodiment of the present invention, the trimethylamine binder is sulfur dioxide or a compound which generates sulfur dioxide upon its dissolution in water (i.e. sulfur dioxide donors). The sulfur dioxide is able to bind trimethylamine after its formation to prevent it from escaping as a gas detectable by the nose. Thus, sulfur dioxide can function like the conjugated base of a weak acid to prevent or reduce the odor of ergothioneine during storage.

SUMMARY OF THE INVENTION

In accordance with a first aspect of the present invention, there is provided an aqueous-containing treatment composition comprising ergothioneine wherein the improvement is supplying the ergothioneine to the treatment composition in the form of a pre-blend comprising ergothioneine and at least one trimethylamine absorber in an amount sufficient to ameliorate any trimethylamine odor in the treatment composition when it is used for its intended purpose.

In accordance with a further aspect of the invention, there is provided a preblend composition consisting essentially of ergothioneine at a concentration of greater than 2 mM (w/v) and a trimethylamine absorber.

In accordance with yet a further aspect of the invention, methods are provided for ameliorating a fishy, amine odor, due to trimethylamine, formed in aqueous solutions, associated with the processing or storage of a preparation containing ergothioneine. Contemplated is a method comprising combining with the ergothioneine, during the processing and/or prior to the storage of the aqueous containing preparation, a trimethylamine absorber in an amount sufficient to ameliorate the detection of the fishy, amine odor in the composition when it used for its intended purpose. Also contemplated is a method comprising introducing into an aqueous containing preparation, after development of the odor, a trimethylamine absorber in an amount sufficient to ameliorate the detection of a fishy, amine odor, due to trimethylamine, by the human nose. Further methods for ameliorating the trimethylamine odor include a method of maintaining an aqueous-containing ergothioneine-containing preparation at a pH of 7 or less, and a method of maintaining the aqueous-containing ergothioneine-containing preparation at a temperature of 25° C. or less.

BRIEF DESCRIPTION OF THE DRAWING

The FIGURE is a schematic drawing of the chemical structure of ergothioneine.

DETAILED DESCRIPTION OF THE INVENTION AND ITS PREFERRED EMBODIMENTS

As described in detail below, in certain of its preferred aspects, the invention provides ergothioneine and ergothioneine-containing mixtures which retain an innocuous odor during preparation and/or storage, and methods for preventing the formation of a fishy, amine odor, due to trimethylamine in ergothioneine and ergothioneine-containing mixtures, or for reducing, minimizing or substantially eliminating the fishy, amine odor, due to trimethylamine, from ergothioneine or ergothioneine-containing mixtures after formation of the odor.

All expressions of percent concentration of ergothioneine herein mean percent weight by volume, unless otherwise explicitly stated.

There are several methods for reducing, minimizing or preventing the formation of the fishy, amine odor from an ergothioneine containing mixtures. The odor can be minimized by reducing levels of ergothioneine. A solution containing ergothioneine in an aqueous medium (or in a non-aqueous polar solvent, such as ethanol, butylene glycol, ethylene glycol, ethylene glycol, isopropanol, or similar monohydric alcohol) at less than about 20 µM (0.00046%), for example, a solution at 0.00001% or less does not produce the characteristic odor.

The formation of the trimethylamine odor also can be minimized during manufacturing of ergothioneine or ergothioneine containing mixtures by maintaining at all times an acidic pH, specifically a pH equal to or less than 7.0, during manufacturing and in the final product. The lower the pH, the less likely is the formation of the odor. A condition of alkalinity, meaning a pH greater than 7.0, even for a brief time, is to be avoided.

In another method, the formation of the trimethylamine odor can be minimized by avoiding heating ergothioneine or the ergothioneine containing mixture above ambient temperature, specifically 25° C., even for brief periods of time. This is particularly the case if sodium hydroxide or other strong or weak base is contained in or added to the ergothioneine containing mixture, or if the mixture is alkaline, meaning pH≥8.0. For long-term storage of ergothioneine or ergothioneine containing mixtures, the odor can be minimized or prevented by maintaining the mixture at or below ambient temperatures, specifically at refrigerated temperatures of about 2-8° C. or at freezing temperatures of about −20° C. to −70° C. In this case, ergothioneine is added in the last step, or in a step near the end, of the manufacturing procedure, after all other components have been added, the mixture is cool and the pH has been appropriately adjusted.

The trimethylamine odor can be minimized during manufacturing by avoiding adding ergothioneine or an ergothioneine-containing mixture to a mixture with sodium hydroxide or other strong or weak base, even if the resulting mixture is neutralized soon after.

The formation of the fishy, amine odor, due to trimethylamine, can be minimized or eliminated by adding to the ergothioneine or the ergothioneine-containing mixture a trimethylamine binder or absorber, more particularly, an acid. The preferred acid is a weak acid. A weak acid is an acid that does not ionize in solution to a significant extent. The $K_a$ (acid dissociation constant, equal to the product of the concentrations of the hydronium ion and the conjugated base divided by the concentration of the undissociated acid) for a weak acid is between $1.8 \times 10^{-16}$ and 55.5. If an acid can release more than one hydronium ion, a separate $K_a$ is calculated for each hydronium ion. Acids with $K_a$ greater than 55.5 are strong acids and almost totally dissociate in water. A specifically preferred acid is one having a $K_a$ between $1.8 \times 10^{-16}$ and $5.5 \times 10^{-1}$, more preferably, an acid having a $K_a$ between $1.82 \times 10^{-1}$ and $1.62 \times 10^{-12}$. Most preferred is citric acid. However, other weak acids useful in the present invention include, but are not limited to, other alpha-hydroxy acids, such as, lactic, glycolic, malic and tartaric acids; carboxylic acids, for example, acetic, butanoic, formic, heptanoic, hexanoic, octanoic, oxalic, pentanoic, propanoic acids; other organic acids, for example, sugar acids, such as, ascorbic acid, and purines, for example, uric acid; inorganic acids, such as boric, carbonic, chromic, hydrocyanic, hydrofluoric, nitrous, phosphoric acid, sulfuric and sulfurous acids, can be used. The amount of the acid used should be sufficient to prevent the detection of the fishy, trimethylamine odor, and this amount for a specific weak acid can be determined by one ordinarily skilled in the art. The ratio of the weight of the acid to the weight of ergothioneine may be in the range of from about 1:1 to about 6:1. Preferably the ratio is greater than about 1:1, such as from about 2:1 to about 4:1, and more preferably, the ratio is about 4:1, respectively.

A particular category of compounds that is useful in preventing, reducing or minimizing the formation of the fishy, trimethylamine odor includes sulfur dioxide and sulfur dioxide donors; that is, compounds that release sulfur dioxide upon dissociation. Examples of such compounds are sodium sulfite, sodium bisulfate, sodium metabisulfite, potassium bisulfate or potassium metabisulfite, and calcium bisulfate. Sulfur dioxide gas may be used directly. In this case the pre-blend of ergothioneine and sulfur dioxide or sulfur dioxide donor compound may comprise from about 0.000001 to about 45%, preferably from about 0.00001 to about 30%, more preferably from about 0.0001 to about 20% ergothioneine, and from about 0.000001 to about 90%, preferably from about 0.00001 to about 60%, and more preferably from about 0.0001 to about 40% of the trimethylamine absorber, in solution, suspension, or emulsion of an aqueous or non-aqueous polar solvent which may be water or butylene glycol, propylene glycol, ethanol, propanol, isopropanol, and so on. In one preferred embodiment, a ratio of about 1:4 ergothioneine:sodium metabisulfite is most preferred.

While the acids, including weak acids, and sulfur dioxide or sulfur dioxide releasing compounds may be used to prevent or minimize the formation of the fishy, trimethylamine odor, they may also be used to minimize or eliminate the odor after its formation. This is believed to be due, in part or in whole, to the ability of the weak acid and/or sulfur dioxide to bind trimethylamine gas and retain it within the ergothioneine containing mixture.

In general, the weaker the acid the stronger it binds trimethylamine, and therefore the better it is at suppressing the fishy, trimethylamine odor. The weakness of an acid is measured by its $K_a$ (acidity constant). The smaller the $K_a$ the weaker the acid. A table of some common acids and their $K_a$ for each of their ionized forms is shown in Table 1. The indicia "E-x", with x referring to a number, means exponent. For example, with respect to acetic acid, 1.74 E-5 means $1.74 \times 10^{-5}$.

TABLE 1

Acids and their $K_a$ values

| ACID | FORMULA | $K_a$ |
| --- | --- | --- |
| acetic acid | H(C2H3O2) | 1.74E−5 |
| ascorbic acid (1) | H2(C6H6O6) | 7.94E−5 |
| ascorbic acid (2) | (HC6H6O6)− | 1.62E−12 |
| boric acid (1) | H3BO3 | 5.37E−10 |
| boric acid (2) | (H2BO3)− | 1.8E−13 |
| boric acid (3) | (HBO3)= | 1.6E−14 |
| butanoic acid | H(C4H7O2) | 1.48E−5 |
| carbonic acid (1) | H2CO3 | 4.47E−7 |
| carbonic acid (2) | (HCO3)− | 4.68E−11 |
| chromic acid (1) | H2CrO4 | 1.82E−1 |
| chromic acid (2) | (HCrO4)− | 3.24E−7 |
| citric acid (1) | H3(C6H5O7) | 7.24E−4 |
| citric acid (2) | (H2C6H5O7)− | 1.70E−5 |
| citric acid (3) | (HC6H5O7)= | 4.07E−7 |
| formic acid | H(CHO2) | 1.78E−4 |
| heptanoic acid | H(C7H13O2) | 1.29E−5 |
| hexanoic acid | H(C6H11O2) | 1.41E−5 |
| hydrocyanic acid | HCN | 6.17E−10 |
| hydrofluoric acid | HF | 6.31E−4 |
| lactic acid | H(C3H5O3) | 8.32E−4 |
| nitrous acid | HNO2 | 5.62E−4 |
| octanoic acid | H(C8H15O2) | 1.29E−4 |
| oxalic acid (1) | H2(C2O4) | 5.89E−2 |
| oxalic acid (2) | (HC2O4)− | 6.46E−5 |
| pentanoic acid | H(C5H9O2) | 3.31E−5 |
| phosphoric acid (1) | H3PO4 | 6.92E−3 |
| phosphoric acid (2) | (H2PO4)− | 6.17E−8 |
| phosphoric acid (3) | (HPO4)= | 2.09E−12 |
| propanoic acid | H(C3H5O2) | 1.38E−5 |
| sulfuric acid (2) | (HSO4)− | 1.05E−2 |
| sulfurous acid (1) | H2SO3 | 1.41E−2 |

TABLE 1-continued

Acids and their $K_a$ values

| ACID | FORMULA | $K_a$ |
|---|---|---|
| sulfurous acid (2) | $(HSO_3)^-$ | 6.31E−8 |
| uric acid | $H(C_5H_3N_4O_3)$ | 1.29E−4 |

Other factors which may be considered, for purposes of commercialization, in the selection of a compound, particularly the weak acid, that meets the requirements of this invention, include the pH of the mixture at the concentration of the weak acid required to minimize, prevent or eliminate the odor, the compatibility of the compound with other components of the mixture, side effects of the compound, regulations of the government or other authorities controlling the compound or its use, the cost of the compound, side reactions of the compound with other components of the mixture or with parts of the human body, or the taste, smell or feel of the compound. For example, oral products containing sulfites, such as sodium metabisulfite, produce allergic reactions in some persons, and therefore in some stocks, intermediate products or finished products this may not be the most favorable compound of the invention. As another example, sodium dioxide is a highly reactive gas and has a characteristic odor, and therefore in some circumstances may not be the preferable compound for use in minimizing, prevention or eliminating the fishy, trimethylamine odor.

The invention can be used with ergothioneine or ergothioneine-containing mixtures such as pure ergothioneine, or a pre-blend comprising ergothioneine in an aqueous or organic solution or emulsion that results from manufacturing, or that constitute the form of shipment or transfer of ergothioneine from one place to another. The pre-blend preferably comprises from about 0.000001 to about 45%, preferably from about 0.00001 to about 30%, more preferably from about 0.0001 to about 20% ergothioneine, and from about 0.000001 to about 90%, preferably from about 0.00001 to about 60%, and more preferably from about 0.0001 to about 40% of the trimethylamine absorber, in solution, suspension, or emulsion with a polar solvent which may be a polar aqueous solvent such as water, or a mixture of water and non-aqueous polar solvents such as $C_{1-4}$ monohydric alcohols, or $C_{1-4}$ dihydric alcohols (such as ethanol, propanol, isopropanol, glycerol, butylene glycol, propylene glycol) where in said polar solvent is present in an amount ranging from about 10 to about 99.99999%, with all percentages mentioned herein being percentages by weight unless otherwise indicated. The pre-blend may contain other ingredients such as preservatives, antioxidants, or other ingredients which enhance stability or provide other commercially beneficial effects. The ergothioneine-containing composition may be sold in the form of the pre-blend to manufacturers of cosmetic, pharmaceutical, or OTC products for their use in formulating such products. The presence of the trimethylamine absorber in the pre-blend ameliorates any unpleasant odor in the pre-blend as well as when it is formulated into cosmetic or pharmaceutical products or otherwise used for its intended purpose.

The invention can also be used in preparation of ergothioneine in aqueous or organic solution or emulsion in products as finished goods. These products can include skincare products, consumer products, over the counter products, oral supplements, nutritional supplements, food, seasoning for food, or pharmaceutical drugs. The products can be used by topical application, subcutaneous injection, intramuscular injection, intravenous injection or any other injection, or by oral or nasal ingestion, or by eye or ear drops, or by suppositories. The nutritional supplements can be for oral ingestion including pills, juices, shakes, power drinks, fortified foods and fortified or supplemented water.

The ergothioneine may be in a pure form before making use of this invention. The ergothioneine may also be in the form of a pre-blend or in a mixture with other compounds. Most preferred is where the ergothioneine will be present in the pre-blend compositions in the amount of from equal to or greater than about 2 mM (0.046% w/v), for example, from about 2 mM to about 70 mM, preferably equal to or greater than about 3 mM, for example, from about 3 mM to about 50 mM, and more preferably, equal to or greater than about 4 mM, for example from about 4 mM to about 30 mM. Compositions into which ergothioneine may be incorporated may be emulsions, solutions, suspensions, gels, or anhydrous compositions. If emulsions, they may be water-in-oil or oil-in-water, comprising from about 0.1 to 95%, preferably from about 0.5 to about 90%, and more preferably from about 1 to 85% water, by weight of the total composition. If in the form of aqueous solutions, suspensions or gels, the composition may contain from about 10 to about 99% water with the remaining ingredients being one or more actives. The ergothioneine or the pre-blend may be solubilized or dispersed in either the aqueous phase or the oil phase of the emulsion. In one preferred embodiment, the ergothioneine is solubilized or dispersed in the aqueous phase. The compositions of the present invention may be in a non-aqueous or anhydrous form in which the ergothioneine is solubilized or dispersed in a polar non-aqueous solvent, such as ethanol, propylene glycol, butylene glycol, or non-polar oils, and the like.

In the event the compositions of the invention into which the ergothioneine is incorporated, either neat or in the form of the pre-blend, are in emulsion form, the composition will comprise an oil phase. Oily ingredients are desirable for the skin moisturizing and protective properties. Suitable oils include silicones, esters, vegetable oils, including but not limited to those set forth herein. The oils may be volatile or nonvolatile, and are preferably in the form of a pourable liquid at room temperature. The term "volatile" means that the oil has a measurable vapor pressure or a vapor pressure of at least about 2 mm. of mercury at 20° C. The term "nonvolatile" means that the oil has a vapor pressure of less than about 2 mm. of mercury at 20° C.

Cyclic silicones are one type of volatile silicone that may be used in the composition. Such silicones have the general formula:

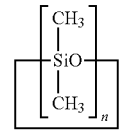

where n=3-6, preferably 4, 5, or 6.

Also suitable are linear volatile silicones, for example, those having the general formula:

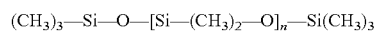

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, 345 and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C. A preferred cyclic volatile silicone is cyclopentasiloxane, available from Dow Corning as DC 345 Fluid.

Suitable branched volatile silicones include alkyl trimethicones such as methyl trimethicone, a branched volatile silicone having the general formula:

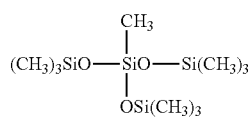

Methyl trimethicone may be purchased from Shin-Etsu Silicones under the tradename TMF-1.5, having a viscosity of 1.5 cst at 25° C.

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

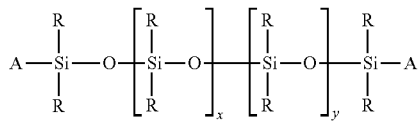

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Preferred is dimethicone which can be purchased from Dow Corning Corporation as DC 200/100 cs fluid.

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to esters and hydrocarbon oils.

Suitable esters are mono-, di-, and triesters. The composition may comprise one or more esters selected from the group, or mixtures thereof.

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, stearyl lactate, stearyl octanoate, stearyl stearate, isononyl isononanoate, and so on.

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

Surface active agents which may be used in the compositions of the invention include silicone surfactants and organic nonionic surfactants. If used, surface active agents are present in the range of from about 0.1 to about 80%, preferably in the range of from about 1 to 50%, and more preferably in the range of from about 5 to about 40%, based on the total weight of the composition.

Suitable silicone surfactants include polyorganosiloxane polymers that have amphiphilic properties, for example contain hydrophilic radicals and lipophilic radicals. These silicone surfactants may be liquids or solids at room temperature.

One type of silicone surfactant that may be used is generally referred to as dimethicone copolyol or alkyl dimethicone copolyol. This surfactant is either a water-in-oil or oil-in-water surfactant having a Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

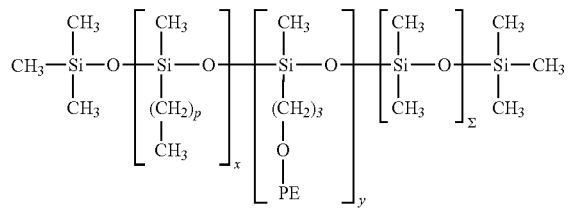

wherein p is 0-40 (the range including all numbers between and subranges such as 2, 3, 4, 13, 14, 15, 16, 17, 18, etc.), and PE is $(\text{—}C_2H_4O)_a\text{—}(\text{—}C_3H_6O)_b\text{—}H$ wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol. One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of crosslinked silicone surfactants that are often referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organopolysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986 and U.S. Pat. No. 5,412,004, U.S. Pat. No. 5,837,793 and U.S. Pat. No. 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer, which provides excellent aesthetics due to its elastomeric backbone, but also surfactancy properties.

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Also suitable as nonionic surfactants are those formed by the reaction of a carboxylic acid with an alkylene oxide or with a polymeric ether. The resulting products have the general formula:

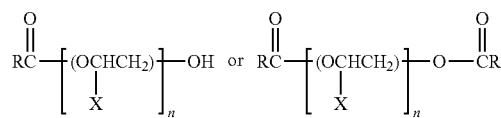

where RCO is the carboxylic ester radical, X is hydrogen or lower alkyl, and n is the number of polymerized alkoxy groups. In the case of the diesters, the two RCO-groups do not need to be identical. Preferably, R is a C6-30 straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula:

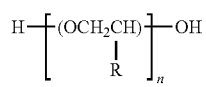

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with $C_{6-30}$, preferably $C_{12-22}$ fatty acids. Examples of such ingredients include Polysorbates 20-85, more specifically Polysorbate 80, sorbitan oleate, sorbitan sesquioleate, sorbitan palmitate, sorbitan sesquiisostearate, sorbitan stearate, and so on. Specifically preferred for use in the present invention is Polysorbate 80, available as Liposorb 0-20 from Lipo Chemicals.

Other compounds which may be found in the compositions of the present invention include, but are not limited to: buffers and salts to adjust the pH of the solution; preservatives and anti-microbial agents, such as Botanistat PF-64, available from D-D Chemco, Inc.; agents that restore the antioxidant capacity of ergothioneine such as forms of Vitamin C; other antioxidants, such as DNA repair extracts encapsulated in liposomes, such as Roxisomes® (Arabidposis Exact/lecithin/water/phenoxyethanol), Ultrasomes® (Micrococcus lysate); vitamins such as vitamin A or vitamin E; nutrients both essential and non-essential, such as amino acids and minerals; compounds for brightening and lighting skin such as undecylenoyl phenylalanine, available as Sepiwhite MSH from Seppic, and mulberry extract; compounds for preventing and reducing irritation and inflammation, such as Evodiox (Evodia Rutaecapra Fruit Extract/butylene glycol/phenoxyethanol); compounds for preventing or slowing aging; compounds that protect against environmental insult and toxins such as ultraviolet light and pollution; compounds for treating disease or cancer; and compounds for preventing disease such as vaccines. It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. The humectants used in the composition of the invention may be $C_{1-6}$, preferably $C_{2-4}$ alkylene glycols, such as butylene glycol. A preferred humectant used in the compositions of the invention is glycerin. These other compounds will be present in the range of from about 0.0001 to about 40% by weight of the composition.

Mixtures of ergothioneine with compounds not listed here may also make use of the invention.

Without intending to restrict in any way the scope of the invention, the following examples are presented to illustrate the invention's aspects and its use.

Example 1

Stability of Ergothioneine with and without Citric Acid

A sample of ergothioneine was prepared at 2 mM or 0.046% (w/v) in water with or without 0.2% (w/v) citric acid and placed in glass vials of approximately 2 ml volume, purged of air with nitrogen gas and sealed. The samples were stored at 4° C., 25° C. or 40° C. for 30 or 60 days and then analyzed by HPLC. Each vial was used once and then discarded. Each measurement was made in triplicate and the results averaged. A standard curve of ergothioneine concentration was constructed at each time point to quantify the amount of ergothioneine in each vial. Each amount in Table 2 is expressed as percentage of the amount measured in the initial sample at the start of the experiment.

TABLE 2

Stability of ergothioneine during storage with and without citric acid as a percent of the starting concentration

| Temperature | Time | % EGT without citric acid | % EGT with citric acid |
|---|---|---|---|
| 4° C. | 30 days | 96.1 | 101.6 |
| 4° C. | 60 days | 106.5 | 105.8 |
| 25° C. | 30 days | 84.0 | 101.5 |
| 25° C. | 60 days | 100.5 | 102.2 |
| 40° C. | 30 days | 86.3 | 101.1 |
| 40° C. | 60 days | 99.8 | 99.6 |

While there was some variability in the measurement of ergothioneine without citric acid at 30 days, the results from the 60 day tests indicate little or no loss of ergothioneine (decomposition or disassociation) during the incubation at temperatures up to 40° C. and no effect of citric acid on the change in ergothioneine concentration.

Example 2

Development of Fishy Amine Odor at Room Temperature Storage

Lotions containing from 20 μM (0.00046%) to 13 mM (0.3%) ergothioneine (w/v) developed a similar fishy, amine odor over time stored at ambient room temperature. These odors were not immediately detected by smelling the container, but were detected after application to the skin and allowing a few seconds before smelling. Another lotion surprisingly did not.

TABLE 3

Formula 1: Lotion

| PHASE | INGREDIENT | % (w/v) |
|---|---|---|
| 1 | Water | 61.80 |
| 1 | Butylene Glycol | 2.00 |
| 1 | Phenoxyethanol | 0.50 |
| 1 | Disodium EDTA | 0.10 |
| 1 | Magnesium Aluminum Silicate | 10.00 |
| 2 | *Simmondsia Chinensis* (Jojoba) Butter | 4.00 |
| 2 | Hydrogenated Polyisobutene | 3.00 |
| 2 | Neopentyl Glycol Dihptanoate | 5.00 |
| 2 | Cetearyl Alcohol/Ceteareth-20 | 01.50 |
| 2 | Cetyl Alcohol | 01.75 |
| 2 | Stearyl Alcohol | 00.70 |
| 2 | Tetrahexyldecyl Ascorbate | 00.50 |
| 2 | Stearic Acid | 00.85 |
| 2 | Glyceryl Stearate/PEG-100 Stearate | 05.00 |
| 2 | 1,2 Hexanediol/Capryl Glycol | 01.00 |
| 3 | Water | 02.00 |
| 3 | Ergothioneine | 00.30 |
| | Total | 100.00 |

Procedure:
Combine phase 1 ingredients in main beaker and heat to 78-80° C. with moderate speed propeller mixing. Combine phase 2 ingredients and heat to 80° C. and mix until clear and uniform. Slowly add phase 2 to phase 1 with moderate speed propeller mixing. Cool batch to 40° C. Then add premixed phase 3 ingredients to the batch. Cool to 25° C. Batch has a final pH of about 4.8-5.2, and a viscosity of about 180,000-230,000 cps. The preparation of this 0.3% ergothioneine in water and magnesium aluminum silicate base lotion, included a manufacturing step in which the ergothioneine phase was added to a 40° C. solution and then cooled to 25° C. It had no odor immediately after manufacturing but developed a noticeable fishy trimethylamine odor after less than a year in storage at ambient temperature.

TABLE 4

Formula 2: Lotion

| PHASE | INGREDIENT | % (w/v) |
|---|---|---|
| 1 | Water | 61.45 |
| 1 | Glycerin | 5.00 |
| 1 | Disodium EDTA | 0.05 |
| 1 | Phenoxyethanol | 0.50 |
| 1 | Carbomer | 12.50 |
| 2 | Steareth-21 | 0.50 |
| 2 | Steareth-2 | 0.10 |
| 2 | Glyceryl Stearate SE | 0.50 |
| 2 | Cetearyl alcohol/Polysorbate 60 | 1.00 |
| 2 | Dimethicone | 4.00 |
| 2 | Cetyl Alcohol | 2.50 |
| 2 | Hydrogenated Coco-glycerides | 1.50 |
| 2 | *Santalum Album* (Sandalwood) Wood Extract/ *Phellodendrom Amurense* Bark Extract/ *Hordeum Distichon* (Barley) Extract | 3.00 |
| 2 | 1,2 Hexanediol/Caprylyl Glycol | 1.00 |
| 3 | Sodium Hydroxide | 0.03 |
| 4 | Polyacrylamide/C13-14 Isoparaffin/Laureth-7 | 2.00 |
| 5 | *Evodia Rutaecarpa* Fruit Extract/Butylene Glycol/Phenoxyethanol | 0.30 |
| 5 | Rosemary Extract/Lecithin/Water | 0.30 |
| 5 | Ergothioneine | 1.00 |
| 5 | Retinol/Polysorbate-20/Lecithin/Water | 1.00 |
| 6 | Sodium Hydroxide (adjust pH to 7.0-7.5) | qs |
| | Total | 100.00 |

Procedure: Combine phase 1 ingredients and heat to 78-80° C. with moderate speed propeller mixing. Mix until carbomer has completely dispersed. Separately, heat phase 2 ingredients to 80° C. and mix until clear and uniform. Add phase 2 to phase 1 with medium speed propeller mixing. Add phase 3 to the batch with medium speed propeller mixing. Cool the batch. At 50° C., add phase 4 to the batch and increase the mixing speed as the batch begins to thicken. At 30-35° C., add phase 5 ingredients individually to the batch. Mix well between the additions. Cool batch to 25° C. and adjust pH to 7.0-7.5 using phase 6 ingredient. The final viscosity of the batch is about 1,125,000-1,375,000 cps. The preparation of this 0.00046% ergothioneine product in water and hydrogel base lotion had no odor immediately after manufacturing but developed a slight fishy, trimethylamine odor after approximately one year in storage at ambient temperature.

TABLE 5

Formula 3: Lotion

| PHASE | INGREDIENT | % (w/v) |
|---|---|---|
| 1 | Water | 70.95 |
| 1 | Glycerin | 2.50 |
| 1 | Disodium EDTA | 0.10 |

TABLE 5-continued

Formula 3: Lotion

| PHASE | INGREDIENT | % (w/v) |
|---|---|---|
| 1 | 1,2 Hexanediol/Caprylyl Glycol | 1.00 |
| 1 | Sodium Hydroxide | 0.50 |
| 2 | C20-22 Alkyl Phosphate/C20-22 Alcohols | 3.00 |
| 2 | Squalane | 3.50 |
| 2 | Cetyl Alcohol | 1.75 |
| 2 | Linoleic Acid | 0.25 |
| 2 | Tocopherol | 0.20 |
| 2 | Tetrahexyldecyl Ascorbate | 0.50 |
| 2 | Hydrogenated Coco-Glycerides | 1.25 |
| 2 | *Glycine Soja* (Soybean) Oil | 2.25 |
| 2 | Isocetyl Stearate | 5.25 |
| 3 | Sodium Acrylate/Acrylyloyldimethyl Taurate/Copolymer/Isohexadecane/Polysorbate 80 | 1.00 |
| 3 | Cyclopentasiloxane | 4.00 |
| 3 | Phenoxyethanol | 0.50 |
| 4 | Ergothioneine | 1.00 |
| 4 | *Arabidposis* Extract/Lecithin/Water/Phenoxyethanol | 0.50 |
| | Total | 100.00 |

Procedure: Combine phase 1 ingredients and heat to 78-80° C. with medium speed propeller mixing. Separately combine phase 2 ingredients and heat to 80° C. Mix until clear and uniform. Add phase 2 to phase 1 with medium speed propeller mixing. Cool batch. At 50° C., add phase 3 ingredients to batch, one at a time, mixing well after each addition. Increase mixing speed as batch begins to thicken. At 25-30° C., add phase 4 ingredients to the batch. Cool batch to 25° C. The final pH of the batch is about 4.6-5.0. The viscosity is about 13,500-16,500 cps. The preparation of this 0.00046% ergothioneine in a water, glycerin and silicone base lotion included a manufacturing step in which ergothioneine was added at the end of the process at 25° C. It developed a very faint fishy trimethylamine odor after approximately one year in storage at ambient temperature.

TABLE 6

Formula 4: Cream

| PHASE | INGREDIENT | % (w/v) |
|---|---|---|
| 1 | Cyclopentasiloxane | 7.00 |
| 1 | Cyclopentasiloxane/PEG/PPG-18/18 Dimethicone | 10.00 |
| 1 | Dimethicone | 2.00 |
| 1 | Polysorbate 80 | 0.50 |
| 1 | Phenoxyethanol/Caprylyl Glycol/Ethylhexylglycerin/Hexylene Glycol | 1.00 |
| 2 | Water | 66.10 |
| 2 | Glycerin | 6.00 |
| 2 | Disodium EDTA | 0.10 |
| 2 | Sodium Metabisulfite | 0.10 |
| 2 | Hydroquinone | 4.00 |
| 2 | Ergothioneine | 0.30 |
| 3 | *Micrococcus lysate* | 1.00 |
| 3 | *Arabidposis* Extract/Lecithin/Water/Phenoxyethanol | 1.00 |
| 3 | *Evodia Rutaecapra* Fruit Extract/Butylene Glycol/Phenoxyethanol | 1.00 |
| | Total | 100.00 |

Procedure: Combine phase 1 ingredients in main kettle and mix until uniform. In side kettle, combine phase 2 ingredients and heat to 40° C. Very slowly add phase 2 to phase 1 and mix well. The rate of addition determines emulsion stability and viscosity. Therefore, phase 2 is best introduced to phase 1 using a funnel to control rate. A rate of 2.5-3 g/minute was used in this 1 kilo lab batch. Slowly add phase 3 ingredients, one at a time, to the batch, mixing well after each addition. Switch to a Silverson mixer, and mix for 1-3 minutes at about 2500-3500 rpm. The product has a final pH of about 6.2 and a viscosity of about 90,000-110,000 cps. The preparation of this 0.3% ergothioneine in a water and silicone base lotion, included manufacturing steps in which no NaOH was used, and ergothioneine was added with sodium metabisulfite at 40° C. It did not develop any fishy, amine smell after storage at 50° C. for 60 days, or over one year storage at ambient temperatures.

Example 3

Formation of Fishy Amine Odor by Addition of Sodium Hydroxide

Four samples of a 5 ml ergothioneine solution at 0.1% (w/v) were prepared in glass test tubes with screw caps. To the first was added 5 ml of water, to the second 5 ml of 0.2% (w/v) sodium metabisulfite, to the third 4 ml of water and 1 ml of 1N sodium hydroxide, and to the fourth 5 ml of 0.2% (w/v) citric acid. The pH of each sample was measured using litmus paper, and they were all pH 5, except for the third sample which had a pH of approximately 10. The samples were boiled for 10 minutes and each one was smelled. The third tube, with sodium hydroxide, had the fishy, amine odor characteristic of ergothioneine solutions after extended storage. None of the other tubes had this odor.

This experiment replicated the appearance of the fishy amine odor using a simple and fast method of briefly boiling with sodium hydroxide. None of the other components alone produced the fishy amine odor. This allowed the testing of methods to inhibit the formation of the odor and to suppress the odor after formation.

Example 4

Preventing Formation of Trimethylamine Odor by Addition of Compounds Before Heating with Sodium Hydroxide Samples were prepared in glass tubes with screw caps with about 0.05% (w/v) ergothioneine in water, a test sample, at the indicated concentration, and 0.1N NaOH (except for the first tube, in which NaOH was omitted as a negative control). The pH of each sample was determined by litmus paper, and then the tubes capped and placed in a boiling water bath for 10 minutes. The tubes were then cooled to room temperature, and then each one was uncapped and smelled by three testers, each of whom scored the odor. The scores were converted to a scale of 0 (no odor) to 3 (strong fishy trimethylamine odor) and then averaged. A sample of each was then assayed for ergothioneine concentration by the method of Example 1. The results are shown in Table 7.

TABLE 7

Ergothioneine concentration and trimethylamine odor rating in treated samples

| Test sample | Concentration | pH | % EGT (w/v) | Odor |
|---|---|---|---|---|
| None | 0 | 5 | 0.050 | 0.00 |
| NaOH without trimethylamine binder | 0 | 11.5 | 0.052 | 3.00 |

TABLE 7-continued

Ergothioneine concentration and trimethylamine odor rating in treated samples

| Test sample | Concentration | pH | % EGT (w/v) | Odor |
|---|---|---|---|---|
| trimethylamine binders added to NaOH: | | | | |
| Citric Acid | 0.2% | 8 | 0.054 | 0.00 |
|  | 0.05% | 10 | 0.053 | 2.00 |
|  | 0.01% | 10 | 0.052 | 2.33 |
| Ascorbic Acid | 0.2% | 5 | 0.047 | 0.00 |
|  | 0.05% | 10.5 | 0.050 | 1.67 |
|  | 0.01% | 10.5 | 0.050 | 1.33 |
| Boric Acid | 0.2% | 8.5 | 0.052 | 0.00 |
|  | 0.05% | 10 | 0.051 | 1.33 |
|  | 0.01% | 10.5 | 0.050 | 1.33 |
| Acetic Acid | 0.2% | 4 | 0.052 | 0.00 |
|  | 0.05% | 8 | 0.052 | 0.67 |
|  | 0.01% | 10.5 | 0.050 | 1.67 |
| Phosphoric Acid | 0.2% | 2.5 | 0.058 | 0.00 |
|  | 0.05% | 5.5 | 0.054 | 0.33 |
|  | 0.01% | 10.5 | 0.052 | 1.33 |
| Hydrochloric acid | 0.01% | 10 | 0.050 | 0.67 |
|  | 0.0001% | 11.5 | 0.050 | 0.67 |
| Sodium Metabisulfite | 0.2% | 6.5 | 0.029 | 0.00 |
|  | 0.05% | 9.5 | 0.037 | 1.00 |
|  | 0.01% | 10 | 0.044 | 1.67 |

The results show that the appearance of the fishy, amine odor is not related to a measurable change in the concentration of ergothioneine. The formation of the odor can be prevented or reduced by the use of acids, particularly weak acids, and sodium metabisulfite.

The appearance of the odor is generally a function of pH, so that protection against the odor generally occurs at lower pH. At equivalent pH, some acids are more efficacious at protecting against odor formation; for example, boric≥acetic>citric acid at pH 8.0-8.5 At equal concentrations, some acids mixed with 0.1N NaOH produce a solution with a lower pH than others; for example, phosphoric<acetic<ascorbic<citric<boric. This is roughly the order of acid strength. The weaker acids appeared to be able to prevent the formation of the odor at higher pH than stronger acids.

Example 5

Preventing Formation of Fishy Trimethylamine Odor by Addition of Compounds after Heating with Sodium Hydroxide Samples were prepared in glass tubes with screw caps with 2 mM (0.046% w/v) ergothioneine in water and 0.1N NaOH (except for the first sample, from which the NaOH was omitted as a negative control). The tubes were capped and placed in a boiling water bath for 10 minutes, and then cooled to room temperature. The test samples were added to the indicated concentration, mixed and held for a few minutes (e.g. no more than 5 minutes). Then each one was uncapped and smelled by three testers, each of whom scored the odor on a scale of 0 (no odor) to 3 (strong fishy, amine odor) and then averaged. The results are shown in Table 8.

TABLE 8

Odor scores of mixtures containing 2 mM (0.046%) ergothioneine

| Test sample | Concentration | Odor |
|---|---|---|
| None | 0 | 0.00 |
| NaOH without trimethylamine binder | 0 | 3.00 |
| Trimethylamine binder added to NaOH: | | |
| Citric Acid | 0.2% | 1.33 |
|  | 0.05% | 2.33 |
|  | 0.01% | 2.33 |
| Ascorbic Acid | 0.2% | 0.00 |
|  | 0.05% | 1.00 |
|  | 0.01% | 2.67 |
| Boric Acid | 0.2% | 1.67 |
|  | 0.05% | 2.67 |
|  | 0.01% | 2.67 |
| Acetic Acid | 0.2% | 0.00 |
|  | 0.05% | 1.33 |
|  | 0.01% | 1.33 |
| Phosphoric Acid | 0.2% | 0.00 |
|  | 0.05% | 1.00 |
|  | 0.01% | 2.33 |
| Hydrochloric acid | 0.01% | 1.00 |
|  | 0.0001% | 2.00 |
| Sodium Metabisulfite | 0.2% | 1.00 |
|  | 0.05% | 2.00 |
|  | 0.01% | 2.00 |

The results of this experiment show that the test samples, especially the weak acids, may be added after the formation of the odor to prevent or reduce its detection.

Example 6

Prevention of Fishy Amine Odor by Formation of Addition Products with Sulfur Dioxide or Sodium Metabisulfite Examples 4 and 5 show that sodium metabisulfite was able to reduce or eliminate the fishy trimethylamine odor when added either before or after the formation of trimethylamine. However, the amount of ergothioneine detected by HPLC appeared to be significantly reduced after addition of sodium metabisulfite. Further study showed that the apparent reduction in the amount of ergothioneine occurred within 10 minutes at room temperature without boiling, suggesting this may not be a covalent reaction.

Sodium metabisulfite generates sulfur dioxide in solution. It is a convenient source of sulfur dioxide gas, which can be toxic because it is readily converted to sulfuric acid. Sulfur dioxide acts similarly to weak bases in binding to trimethylamine to form a water-soluble and much less volatile trimethylamine addition compound, as described by Bright and Fernelius in 1946. J. Russell Bright and W. Conard Fernelius. "Addition compound of sulfur dioxide and trimethylamine", *Inorganic Syntheses*, Volume II, Chapter VI. Ed. W. Conard Fernelius. McGraw-Hill Book Company, Inc. pp. 159-161, 1946.

The apparent loss of the ergothioneine immediately after addition of sodium metabisulfite is due to the formation of another reversible addition product between sulfur dioxide and ergothioneine, as described by Balaban and King in 1927. Isidore Elkanah Balaban and Harold King. "Gold and mercury derivatives of 2-thiol-glyoxalines. Mechanism of the oxidation of 2-thiolglyoxalines to glyoxalines". *J. Chem. Soc.*

(1927) pp 1858-1874. This addition product, at sufficiently high concentration, has a yellow color.

To demonstrate this chemical reaction, sample vials were prepared with a 1.25% solution of ergothioneine in water with increasing amounts of sodium metabisulfite from 2.5% to 50%. The vials were sealed and mixing the samples was avoided. The samples were incubated and color development observed. The solutions were examined at 1 hour, and the optical density at 405 nm was measured at 2 hours (Table 9). As the concentration of sodium metabisulfite increased, the intensity of the yellow color, and the $OD_{405}$ also increased.

TABLE 9

Formation of yellow color in a solution of ergothioneine and sodium metabisulfite

| Ergothioneine | Sodium metabisulfite | Color description at 1 h | $OD_{405}$ at 2 hr |
| --- | --- | --- | --- |
| 2.5% | 0 | Colorless | 0.004 |
| 1.25% | 2.5% | Colorless | 0.044 |
| 1.25% | 5.0% | Near colorless | 0.104 |
| 1.25% | 7.5% | Yellow tinge | 0.186 |
| 1.25% | 10% | Slight yellow | 0.265 |
| 1.25% | 12.5% | Light yellow | 0.456 |
| 1.25% | 15% | Yellow | 0.593 |
| 1.25% | 17.5% | Yellow | 0.966 |
| 1.25% | 20% | Light lemon yellow | 1.993 |
| 1.25% | 22.5% | Intense lemon yellow | 2.873 |
| 1.25% | 25% | Intense lemon yellow | 3.126 |

It was further observed that the addition product, and hence the yellow color, is entirely reversible by driving off the sulfur dioxide gas. To demonstrate this chemical reaction, a solution of 1.25% ergothioneine and 5% sodium metabisulfite turned intense lemon yellow after one week at room temperature in a capped tube. The cap was removed and the solution was then shaken for 3 to 4 minutes and ambient air was bubbled through it to drive out the dissolved sulfur dioxide gas. After 6 to 7 minutes the solution turned nearly colorless with a yellow tinge. Analysis of the ergothioneine content of the solutions by HPLC shows a reduction in concentration with the formation of the yellow color, and a partial restoration of the ergothioneine concentration with the loss of the yellow color. Therefore the loss of ergothioneine after addition of sodium metabisulfite is due to formation of an addition product which is reversible, and the ergothioneine is not permanently lost.

Example 7

Preventing Formation of Fishy Amine Odor

TABLE 10

Formula 5: Concentrate

| PHASE | INGREDIENT | % (w/v) |
| --- | --- | --- |
| 1 | Cyclopentasiloxane | 10.00 |
| 1 | Cyclopentasiloxane/PEG/PPG-18/18 Dimethicone | 10.00 |
| 1 | Dimethicone | 4.00 |
| 1 | Polysorbate 80 | 0.50 |
| 1 | Phenoxyethanol/Caprylyl Glycol/ Ethylhexylglycerine/Hexylene Glycol | 1.00 |
| 2 | Water | 62.30 |
| 2 | Glycerin | 6.00 |
| 2 | Tetrasodium EDTA | 0.10 |
| 2 | Undecylenoyl Phenylalanine | 2.00 |

TABLE 10-continued

Formula 5: Concentrate

| PHASE | INGREDIENT | % (w/v) |
| --- | --- | --- |
| 2 | Sodium Hydroxide | 1.00 |
| 2A | Ergothioneine | 0.10 |
| 2A | Citric Acid | 0.20 |
| 3 | Sodium Hydroxide | * |
| 3 | Citric Acid | * |
| 4 | Micrococcus lysate | 1.20 |
| 4 | Arabidposis Extract/Lecithin/Water/ Phenoxyethanol | 1.00 |
| 4 | Evodia Rutaecapra Fruit Extract/ Butylene Glycol/Phenoxyethanol | 1.00 |
| | Total | 100.00 |

* (amount sufficient to adjust pH to 6.8-7.4)

Procedure: In the main kettle, combine phase 1 ingredients and mix until uniform. In a side kettle, combine phase 2 ingredients and heat to 65° C. Cool phase 2 to 25° C. and adjust pH to 6.8-7.4 and clear using phase 3 ingredients. At 25° C., add phase 2A ingredients to phase 2 with propeller mixing. Very slowly add phase 2 to phase 1 and mix well. The rate of addition determines emulsion stability and viscosity. It is best added with a funnel to control rate. (A rate of 1-2 g/minute was used in the 1 kilo lab batch.) Slowly add phase 4 ingredients and mix until uniform. Switch to a Silverson mixer, and mix for 1-3 minutes at approximately 2500-3500 rpm. The product has a final pH of about 6.8-7.2, a viscosity of 15,000-20,000 cps and a specific gravity of 1.01±0.02. The preparation of this 0.1% ergothioneine in water and magnesium aluminum silicate base with 0.2% citric acid included a manufacturing step in which the ergothioneine was added in a phase at the end when the formula had cooled to 25° C. It had no odor immediately after manufacturing and did not develop an odor after heating for 60 days at 40° C. or after six months of storage at ambient temperature.

As used herein, "ameliorate" means, with respect to the trimethylamine, to improve the trimethylamine odor by reducing, inhibiting, preventing, or eliminated it; "treatment composition" means a product for use in treatment mammals, and may include ingestible, topical or injectable products; and "pre-blend" means a composition that may be in the form of a solution, suspension, emulsion or anhydrous composition, that is formed separately by combining the ingredients present in the pre-blend, and then incorporating the pre-blend into the treatment composition during the treatment composition formulation process. By use of the term "consisting essentially of", it is intended that the composition or method does not include any component or step which would materially affect the basic and novel characteristics of the invention.

What is claimed is:

1. A method for sequestering trimethylamine released from ergothioneine in a topical, aqueous-containing cosmetic or pharmaceutical composition stored at room temperature prior to application of the composition to skin, said composition having a neutral to acidic pH and comprising greater than 20 µM (w/v) ergothioneine, said method comprising adding to said composition a trimethylamine absorber comprising a weak organic acid in an amount sufficient to bind the trimethylamine so as to prevent development of a fishy odor when the composition is applied to the skin, wherein the trimethylamine absorber is added to the composition before, during or after the storage.

2. The method of claim 1, wherein the weak organic acid added to said topical, aqueous-containing cosmetic or pharmaceutical composition has an acid dissociation constant ($K_a$) of between about $1.8 \times 10^{-16}$ and 55.5.

3. The method of claim 2, wherein the weak organic acid added to said topical, aqueous-containing cosmetic or pharmaceutical composition is selected from the group consisting of acetic acid, ascorbic acid, citric acid, formic acid, heptanoic acid, hexanoic acid, lactic acid, octanoic acid, oxalic acid, pentanoic acid, propanoic acid, uric acid, and mixtures thereof.

4. The method of claim 3, wherein the weak organic acid added to said topical, aqueous-containing cosmetic or pharmaceutical composition is citric acid.

5. The method of claim 1, wherein the weak organic acid and the ergothioneine are present in the topical, aqueous-containing cosmetic or pharmaceutical composition in a ratio in the range of from about 2:1 to about 4:1.

6. The method of claim 1, wherein the topical, aqueous-containing cosmetic or pharmaceutical composition has been stored at room temperature for at least about 60 days.

7. The method of claim 1, wherein the topical, aqueous-containing cosmetic or pharmaceutical composition has been stored at room temperature for about one year.

8. A method for preventing or eliminating development of a fishy odor in a topical, aqueous-containing cosmetic or pharmaceutical product during storage of the product at room temperature, said product having a neutral to acidic pH and comprising greater than 20 μM (w/v) ergothioneine, said method comprising introducing the ergothioneine into the product in the form of a composition comprising ergothioneine at a concentration of greater than 20 mM (w/v) and a trimethylamine absorber comprising a weak organic acid before, during or after storing the product, such that the ergothioneine and the weak organic acid are present in the product in amounts sufficient to permit the weak organic acid to bind trimethylamine released from the ergothioneine during storage of the product.

9. The method of claim 8, wherein the weak organic acid is selected from the group consisting of acetic acid, ascorbic acid, citric acid, formic acid, heptanoic acid, hexanoic acid, lactic acid, octanoic acid, oxalic acid, pentanoic acid, propanoic acid, uric acid, and mixtures thereof.

10. The method of claim 9, wherein the weak organic acid comprises citric acid.

11. The method of claim 8, wherein the weak organic acid and the ergothioneine are present in the product in a ratio in the range of from about 2:1 to about 4:1.

* * * * *